(12) United States Patent
Humphreys et al.

(10) Patent No.: US 7,556,651 B2
(45) Date of Patent: Jul. 7, 2009

(54) POSTERIOR SPINAL DEVICE AND METHOD

(75) Inventors: Steven C. Humphreys, Chattanooga, TN (US); Scott D. Hodges, Ooltewah, TN (US); Marc M. Peterman, Memphis, TN (US); Lukas G. Eisermann, Memphis, TN (US); Randall Allard, Germantown, TN (US)

(73) Assignee: Warsaw Orthopedic, Inc.

( * ) Notice: Subject to any disclaimer, the term of this patent is extended or adjusted under 35 U.S.C. 154(b) by 188 days.

(21) Appl. No.: 11/031,903

(22) Filed: Jan. 7, 2005

(65) Prior Publication Data

US 2005/0154466 A1 Jul. 14, 2005

Related U.S. Application Data

(60) Provisional application No. 60/534,960, filed on Jan. 9, 2004.

(51) Int. Cl.
*A61F 2/44* (2006.01)
(52) U.S. Cl. .................................... 623/17.15
(58) Field of Classification Search .... 623/17.11–17.16
See application file for complete search history.

(56) References Cited

U.S. PATENT DOCUMENTS

| | | | |
|---|---|---|---|
| 4,349,921 A | 9/1982 | Kuntz | |
| 4,697,582 A | 10/1987 | William | |
| 4,759,769 A * | 7/1988 | Hedman et al. | 623/17.13 |
| 5,062,850 A * | 11/1991 | MacMillan et al. | 623/17.11 |
| 5,092,866 A | 3/1992 | Breard et al. | |
| 5,258,031 A * | 11/1993 | Salib et al. | 623/17.15 |
| 5,282,863 A | 2/1994 | Burton | |
| 5,387,213 A | 2/1995 | Breard et al. | |
| 5,401,269 A | 3/1995 | Buttner-Janz et al. | |
| 5,415,661 A | 5/1995 | Holmes | |
| 5,507,816 A | 4/1996 | Bullivant | |
| 5,556,431 A | 9/1996 | Buttner-Janz | |
| 5,562,660 A | 10/1996 | Grob | |
| 5,562,737 A | 10/1996 | Graf | |

(Continued)

FOREIGN PATENT DOCUMENTS

DE 101 35771 A1 2/2003

(Continued)

OTHER PUBLICATIONS

Patent Cooperation Treaty—European Patent Office, "Notification of Transmittal of the International Search Report and the Written Opinion of the Internatinal Searching Authority, or the Declaration," International Application No. PCT/US2005/000648, Jun. 6, 2005, 6 pages.

(Continued)

*Primary Examiner*—William H. Matthews
*Assistant Examiner*—Ann Schillinger

(57) ABSTRACT

An artificial spinal joint for creating at least a portion of a coupling between a superior vertebra and an inferior vertebra comprises a first joint half comprising a first intervertebral articulating assembly, a first rostral connection assembly, and a first caudal connection assembly. The joint further comprises a second joint half comprising a second intervertebral articulating assembly, a second rostral connection assembly, and a second caudal connection assembly. The joint further comprises a constraint component extending between the first rostral connection assembly and the first caudal connection assembly.

38 Claims, 7 Drawing Sheets

U.S. PATENT DOCUMENTS

| | | | |
|---|---|---|---|
| 5,562,738 A | 10/1996 | Boyd et al. | |
| 5,672,175 A | 9/1997 | Martin | |
| 5,676,701 A | 10/1997 | Yuan et al. | |
| 5,702,450 A * | 12/1997 | Bisserie | 623/17.16 |
| 5,728,098 A * | 3/1998 | Sherman et al. | 606/61 |
| 5,895,428 A | 4/1999 | Berry | |
| 5,899,941 A | 5/1999 | Nishijima et al. | |
| RE36,221 E | 6/1999 | Breard et al. | |
| 5,928,284 A * | 7/1999 | Mehdizadeh | 623/17.13 |
| 5,961,516 A | 10/1999 | Graf | |
| 6,039,763 A | 3/2000 | Shelokov | |
| RE36,758 E | 6/2000 | Fitz | |
| 6,106,557 A * | 8/2000 | Robioneck et al. | 623/17.15 |
| 6,113,637 A | 9/2000 | Gill et al. | |
| 6,132,464 A | 10/2000 | Martin | |
| 6,146,421 A | 11/2000 | Gordon et al. | |
| 6,156,067 A | 12/2000 | Bryan et al. | |
| 6,179,874 B1 | 1/2001 | Cauthen | |
| 6,179,875 B1 | 1/2001 | Strempel | |
| 6,228,118 B1 | 5/2001 | Gordon | |
| 6,231,609 B1 * | 5/2001 | Mehdizadeh | 623/17.11 |
| 6,251,112 B1 * | 6/2001 | Jackson | 606/61 |
| 6,368,350 B1 | 4/2002 | Erickson et al. | |
| 6,402,750 B1 | 6/2002 | Atkinson et al. | |
| 6,402,785 B1 * | 6/2002 | Zdeblick et al. | 623/17.16 |
| 6,419,703 B1 | 7/2002 | Fallin et al. | |
| 6,432,140 B1 * | 8/2002 | Lin | 623/17.16 |
| 6,440,168 B1 * | 8/2002 | Cauthen | 623/17.14 |
| 6,454,807 B1 * | 9/2002 | Jackson | 623/17.15 |
| 6,471,724 B2 * | 10/2002 | Zdeblick et al. | 623/17.16 |
| 6,517,580 B1 | 2/2003 | Ramadan et al. | |
| 6,527,804 B1 | 3/2003 | Gauchet et al. | |
| 6,540,747 B1 | 4/2003 | Marino | |
| 6,540,785 B1 * | 4/2003 | Gill et al. | 623/17.14 |
| 6,565,571 B1 | 5/2003 | Jackowshi et al. | |
| 6,565,605 B2 | 5/2003 | Goble et al. | |
| 6,572,653 B1 * | 6/2003 | Simonson | 623/17.13 |
| 6,579,319 B2 | 6/2003 | Goble et al. | |
| 6,582,466 B1 | 6/2003 | Gauchet | |
| 6,582,468 B1 * | 6/2003 | Gauchet | 623/17.16 |
| 6,610,091 B1 | 8/2003 | Reiley | |
| 6,610,093 B1 * | 8/2003 | Pisharodi | 623/17.15 |
| 6,669,729 B2 | 12/2003 | Chin | |
| 6,679,915 B1 | 1/2004 | Cauthen | |
| 6,685,742 B1 * | 2/2004 | Jackson | 623/17.11 |
| 6,699,247 B2 * | 3/2004 | Zucherman et al. | 606/61 |
| 6,733,532 B1 * | 5/2004 | Gauchet et al. | 623/17.12 |
| 6,805,714 B2 * | 10/2004 | Sutcliffe | 623/17.16 |
| 6,908,484 B2 * | 6/2005 | Zubok et al. | 623/17.15 |
| 6,981,989 B1 * | 1/2006 | Fleischmann et al. | 623/17.11 |
| 7,025,787 B2 * | 4/2006 | Bryan et al. | 623/17.16 |
| 7,052,515 B2 | 5/2006 | Simonson | |
| 7,083,649 B2 | 8/2006 | Zucherman et al. | |
| 7,147,665 B1 * | 12/2006 | Bryan et al. | 623/17.16 |
| 2001/0005796 A1 * | 6/2001 | Zdeblick et al. | 623/17.11 |
| 2001/0034553 A1 * | 10/2001 | Michelson | 623/17.11 |
| 2002/0049394 A1 * | 4/2002 | Roy et al. | 600/594 |
| 2002/0052656 A1 * | 5/2002 | Michelson | 623/17.11 |
| 2002/0095154 A1 | 7/2002 | Atkinson et al. | |
| 2002/0107572 A1 * | 8/2002 | Foley et al. | 623/17.11 |
| 2002/0116065 A1 * | 8/2002 | Jackson | 623/17.16 |
| 2002/0123806 A1 | 9/2002 | Reiley | |
| 2002/0128712 A1 * | 9/2002 | Michelson | 623/17.11 |
| 2002/0133155 A1 | 9/2002 | Ferree | |
| 2002/0143399 A1 * | 10/2002 | Sutcliffe | 623/17.11 |
| 2002/0151895 A1 | 10/2002 | Soboleski et al. | |
| 2003/0004572 A1 | 1/2003 | Goble et al. | |
| 2003/0009226 A1 | 1/2003 | Graf | |
| 2003/0028250 A1 | 2/2003 | Reiley et al. | |
| 2003/0040797 A1 | 2/2003 | Fallin et al. | |
| 2003/0055427 A1 | 3/2003 | Graf | |
| 2003/0100949 A1 * | 5/2003 | Michelson | 623/17.11 |
| 2003/0139813 A1 | 7/2003 | Messerli et al. | |
| 2003/0191532 A1 | 10/2003 | Goble et al. | |
| 2003/0199981 A1 | 10/2003 | Ferree | |
| 2003/0199982 A1 | 10/2003 | Bryan | |
| 2003/0204259 A1 | 10/2003 | Goble et al. | |
| 2003/0204260 A1 * | 10/2003 | Ferree | 623/17.11 |
| 2003/0204271 A1 | 10/2003 | Ferree | |
| 2003/0233146 A1 * | 12/2003 | Grinberg et al. | 623/17.14 |
| 2004/0002761 A1 | 1/2004 | Rogers et al. | |
| 2004/0002762 A1 | 1/2004 | Hawkins | |
| 2004/0006391 A1 | 1/2004 | Reiley | |
| 2004/0024462 A1 | 2/2004 | Ferree et al. | |
| 2004/0030390 A1 | 2/2004 | Ferree | |
| 2004/0030391 A1 | 2/2004 | Ferree | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049279 A1 | 3/2004 | Sevrain | |
| 2004/0049281 A1 | 3/2004 | Reiley | |
| 2004/0073311 A1 * | 4/2004 | Ferree | 623/17.14 |
| 2004/0098131 A1 * | 5/2004 | Bryan et al. | 623/17.15 |
| 2004/0102848 A1 * | 5/2004 | Michelson | 623/17.11 |
| 2004/0111161 A1 * | 6/2004 | Trieu | 623/17.16 |
| 2004/0127991 A1 * | 7/2004 | Ferree | 623/17.11 |
| 2004/0138749 A1 | 7/2004 | Zucherman et al. | |
| 2004/0176850 A1 * | 9/2004 | Zubok et al. | 623/17.15 |
| 2004/0181284 A1 | 9/2004 | Simonson | |
| 2004/0181285 A1 | 9/2004 | Simonson | |
| 2004/0193272 A1 * | 9/2004 | Zubok et al. | 623/17.11 |
| 2004/0243241 A1 * | 12/2004 | Istephanous et al. | 623/17.14 |
| 2004/0254643 A1 * | 12/2004 | Jackson | 623/17.11 |
| 2005/0027359 A1 * | 2/2005 | Mashburn | 623/17.11 |
| 2005/0080488 A1 * | 4/2005 | Schultz | 623/17.13 |
| 2005/0143820 A1 | 6/2005 | Zucherman et al. | |
| 2005/0143822 A1 * | 6/2005 | Paul | 623/17.16 |
| 2005/0149189 A1 * | 7/2005 | Mokhtar et al. | 623/17.11 |
| 2005/0154461 A1 | 7/2005 | Humphreys et al. | |
| 2005/0154462 A1 | 7/2005 | Zucherman et al. | |
| 2005/0154464 A1 | 7/2005 | Humphreys et al. | |
| 2005/0154465 A1 | 7/2005 | Hodges et al. | |
| 2005/0154466 A1 | 7/2005 | Humphreys et al. | |
| 2005/0154467 A1 | 7/2005 | Peterman et al. | |
| 2005/0171608 A1 | 8/2005 | Peterman et al. | |
| 2005/0171610 A1 | 8/2005 | Humphreys et al. | |
| 2005/0256578 A1 | 11/2005 | Blatt et al. | |
| 2005/0261774 A1 * | 11/2005 | Trieu | 623/17.16 |
| 2005/0277930 A1 | 12/2005 | Parsons | |
| 2005/0277938 A1 | 12/2005 | Parsons | |
| 2006/0036325 A1 | 2/2006 | Paul et al. | |
| 2006/0069438 A1 | 3/2006 | Zucherman et al. | |
| 2006/0069440 A1 | 3/2006 | Zucherman et al. | |
| 2006/0085076 A1 | 4/2006 | Krishna et al. | |
| 2006/0178745 A1 | 8/2006 | Bartish, Jr. et al. | |

FOREIGN PATENT DOCUMENTS

| | | |
|---|---|---|
| DE | 20 2004 015198 | 11/2004 |
| EP | 0 677 277 A2 | 10/1995 |
| EP | 1 281 361 A1 | 2/2003 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | 0004851 | 2/2000 |
| WO | WO 00/04851 | 2/2000 |
| WO | WO 01/39678 | 6/2001 |
| WO | WO 01/45576 | 6/2001 |

| WO | WO 02/47586 | | 6/2002 |
| --- | --- | --- | --- |
| WO | WO 03/041618 | A2 | 5/2003 |
| WO | WO 03/045262 | A2 | 6/2003 |
| WO | WO 03/084449 | | 10/2003 |
| WO | WO 03/101350 | | 12/2003 |
| WO | 2004034935 | | 4/2004 |
| WO | WO 2004/041131 | | 5/2004 |
| WO | WO 2004/098465 | | 11/2004 |
| WO | WO 2005/112835 | | 12/2005 |

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.

Patent Cooperation Treaty—European Patent Office, "Invitation to Pay Additional Fees/Communication Relating to the Results of the Partial International Search," International Application No. PCT/US2005/000586, Jun. 8, 2005, 5 pages.

Patent Cooperation Treaty—European Patent Office, "Notification of Transmittal of the International Search Report and the Written Opinion of the Internatinal Searching Authority, or the Declaration," International Application No. PCT/US2005/000585, Jun. 8, 2005, 6 pages.

Patent Cooperation Treaty—European Patent Office, "Notification of Transmittal of the International Search Report and the Written Opinion of the International Searching Authority, or the Declaration," International Application No. PCT/US2005/000704, Aug. 23, 2005, 7 pages.

Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.

U.S. Appl. No. 11/343,159, filed Jan. 30, 2006 in the name of Braddock et al.

U.S. Appl. No. 11/342,961, filed Jan. 30, 2006 in the name of Yu et al.

U.S. Appl. No. 11/393,488, filed Mar. 30, 2006 in the name of Yu et al.

U.S. Appl. No. 11/494,311, filed Jul. 27, 2006 in the name of Yu et al.

* cited by examiner

POSTERIOR SPINAL DEVICE AND METHOD

CROSS-REFERENCE

This application claims priority from U.S. Provisional Patent Application Ser. No. 60/534,960 filed on Jan. 9, 2004, entitled "Posterior Lumbar Arthroplasty." The following applications also claim priority to the above referenced provisional application and are related to the present application. They are incorporated by reference herein.

U.S. Utility patent application Ser. No. 11/031,602, filed on Jan. 7, 2005 and entitled "Spinal Arthroplasty Device and Method;"

U.S. Utility patent application Ser. No. 11/031/603, filed on Jan. 7, 2005 and entitled "Dual Articulating Spinal Device and Method;"

U.S. Utility patent application Ser. No. 11/031,780, filed on Jan. 7, 2005 and entitled "Split Spinal Device and Method;"

U.S. Utility patent application Ser. No. 11/031,904, filed on Jan. 7, 2005 and entitled "Interconnected Spinal Device and Method;"

U.S. Utility patent application Ser. No. 11/031,783, filed on Jan. 7, 2005 and entitled "Mobile Bearing Spinal Device and Method;"

U.S. Utility patent application Ser. No. 11/031,700, filed on Jan. 7, 2005 and entitled "Support Structure Device and Method;" and U.S. Utility patent application Ser. No. 11/031,781, filed on Jan. 7, 2005 and entitled "Centrally Articulating Spinal Device and Method."

TECHNICAL FIELD

Embodiments of the invention relate generally to devices and methods for accomplishing spinal surgery, and more particularly in some embodiments, to spinal arthroplasty devices capable of being placed posteriorly into the vertebral disc space. Various implementations of the invention are envisioned, including use in total spine arthroplasty replacing, via a posterior approach, both the disc and facet functions of a natural spinal joint.

BACKGROUND

As is known the art, in the human anatomy, the spine is a generally flexible column that can take tensile and compressive loads, allows bending motion and provides a place of attachment for ribs, muscles and ligaments. Generally, the spine is divided into three sections: the cervical, the thoracic and the lumbar spine. FIG. 1 illustrates schematically the lumbar spinal 1 and the sacrum regions 3 of a healthy, human spinal column. The sections of the spine are made tip of individual bones called vertebrae and the vertebrae are separated by intervertebral discs which are situated therebetween.

FIG. 2 illustrates a portion of the right side of a lumbar spinal region with a healthy intervertebral disc 5 disposed between two adjacent vertebrae 7, 9. In any given joint, the top vertebra may be referred to as the superior vertebra and the bottom one as the inferior vertebra. Each vertebra comprises a generally cylindrical body 7a, 9a, which is the primary area of weight bearing, and three bony processes, e.g., 7b, 7c, 7d (two of which are visible in FIG. 2). As shown in FIG. 7A, in which all of the processes are visible, processes 7b, 7c, 7d extend outwardly from vertebrae body 7 at circumferentially spaced locations. The processes, among other functions, provide areas for muscle and ligament attachment.

Neighboring vertebrae may move relative to each other via facet components 7e (FIG. 2), which extend from the cylindrical body of the vertebrae and are adapted to slide one over the other during bending to guide movement of the spine. There are two facet joints, each defined by upper and lower facet components, associated with adjacent vertebra. A healthy intervertebral disc is shown in FIG. 3. As shown in FIG. 3, an intervertebral disc has 4 regions: a nucleus pulposus 11, a transition zone 13, an inner annulus fibrosis region 15 and an outer annulus fibrosis 17. Generally, the inner annulus fibrosis region 15 and the outer annulus fibrosis region 17 are made up of layers of a fibrous gristly material firmly attached to the vertebral bodies above and below it. The nucleus pulposus 11 is typically more hydrated in nature.

These intervertebral discs function as shock absorbers and as joints. They are designed to absorb the compressive and tensile loads to which the spinal column may be subjected while at the same time allowing adjacent vertebral bodies to move relative to each other a limited amount, particularly during bending (flexure) of the spine. Thus, the intervertebral discs are under constant muscular and/or gravitational pressure and generally are the first parts of the lumbar spine to show signs of "wear and tear".

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

One surgical procedure for treating these conditions is spinal arthrodesis (i.e., spine fusion), which has been performed both anteriorly and/or posteriorly. The posterior procedures include in-situ fusion, posterior lateral instrumented fusion, transforaminal lumbar interbody fusion ("TLIF") and posterior lumbar interbody fusion ("PLIF"). Solidly fusing a spinal segment to eliminate any motion at that level may alleviate the immediate symptoms, but for some patients maintaining motion may be advantageous. It is also known to surgically replace a degenerative disc or facet joint with an artificial disc or an artificial facet joint, respectively. However, none of the known devices or methods provide the advantages of the embodiments of the present disclosure.

Accordingly, the foregoing shows there is a need for an improved spinal arthroplasty that avoids the drawbacks and disadvantages of the known implants and surgical techniques.

SUMMARY

In one embodiment, an artificial spinal joint for creating at least a portion of a coupling between a superior vertebra and an inferior vertebra comprises a first joint half comprising a first intervertebral articulating assembly, a first rostral connection assembly, and a first caudal connection assembly. The joint further comprises a second joint half comprising a second intervertebral articulating assembly, a second rostral connection assembly, and a second caudal connection assembly. The joint further comprises a constraint component extending between the first rostral connection assembly and the first caudal connection assembly.

In another embodiment, a method for installing a bi-lateral artificial spinal joint comprises the steps of accessing an intervertebral disc space through an incision using a surgical approach, positioning a first fastener in a vertebra superior to the intervertebral disc space, and positioning a second fastener in a vertebra inferior to the intervertebral disc space. The method further comprises positioning a rostral articulating component of the bi-lateral artificial spinal joint in the intervertebral disc space and positioning a caudal articulating component of the bi-lateral artificial spinal joint in the intervertebral disc space. The method also comprises connecting the rostral articulating component to the first fastener, connecting the caudal articulating component to the second fastener, and extending a first constraint member between the first fastener and the second fastener.

In another embodiment, an artificial joint system comprises an articulating assembly for interposition in an intervertebral disc space. The articulating assembly comprises a first articulating component movable with respect to a second articulating component. The system further comprises a first bridge component coupled to the first articulating component and extending posteriorly from the intervertebral disc space. The system also comprises a first connection assembly coupled to the first bridge component. The system comprises a second bridge component coupled to the second articulating component and extending posteriorly from the intervertebral disc space. The system comprises a second connection assembly coupled to the second bridge component and a constraint component extending between the first and second connection assemblies.

The embodiments disclosed may be useful for degenerative changes of the lumbar spine, post-traumatic, discogenic, facet pain or spondylolisthesis, and/or to maintain motion in multiple levels of the lumbar spine.

Additional and alternative features, advantages, uses and embodiments are set forth in or will be apparent from the following description, drawings, and claims.

DESCRIPTION

The drawings illustrate various embodiments of an artificial intervertebral joint for replacing an intervertebral disc or the combination of an intervertebral disc and at least one corresponding facet joint. Various embodiments of the artificial intervertebral joint according to the principles of the disclosure may be used for treating any of the problems that lend themselves to joint replacement including particularly, for example, degenerative changes of the lumbar spine, post-traumatic, discogenic, facet pain or spondylolisthesis and/or to maintain motion in multiple levels of the lumbar spine.

Figure 1:
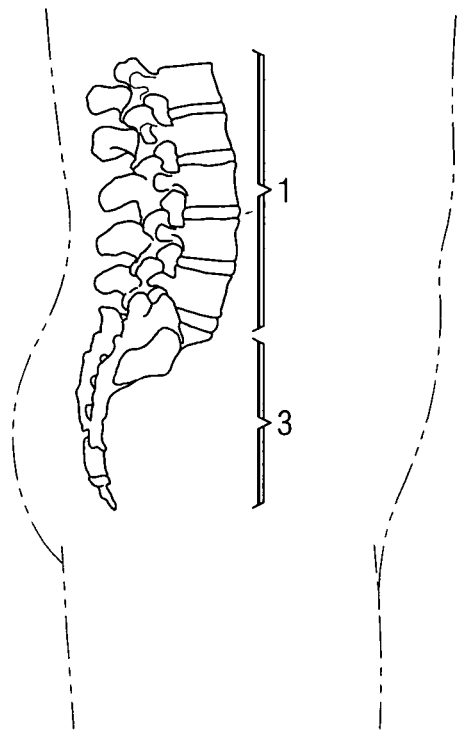
FIG. 1 is a side elevation schematic view of the lumbar spinal and the sacrum regions of a healthy, human spinal column.
Figure 2:
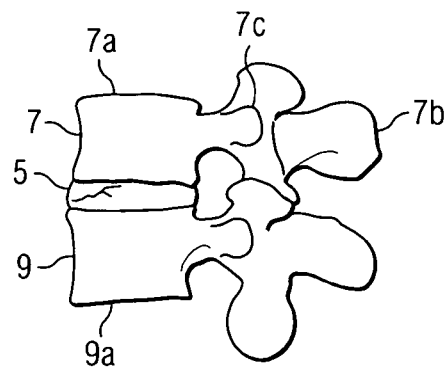
FIG. 2 is a detailed perspective view showing a portion of the right side of the lumbar vertebrae shown in FIG. 1 with a healthy disc disposed between two vertebrae.
Figure 3:
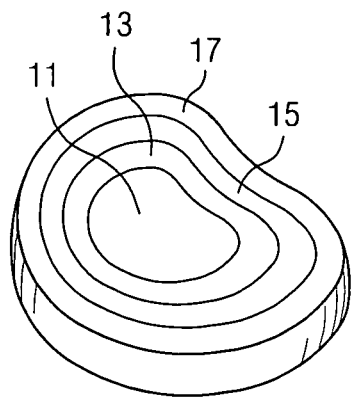
FIG. 3 is a top perspective view of the intervertebral disc shown in FIG. 2 illustrating the major portions of the disc.
Figure 4:
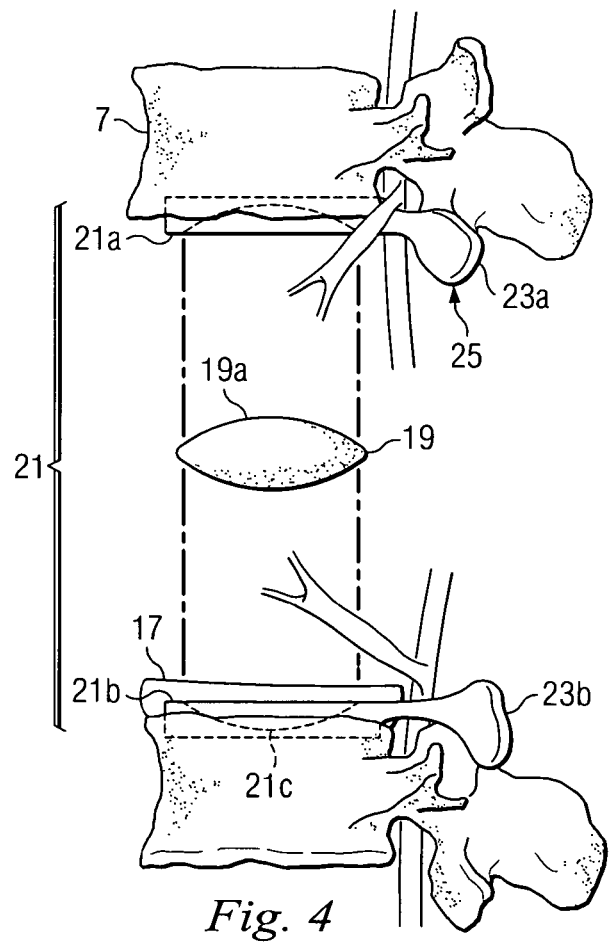
FIG. 4 is a side exploded elevation view of a portion of a lumbar spine showing a first embodiment of an artificial intervertebral joint constructed according to the principles of the disclosure.
Figure 5:
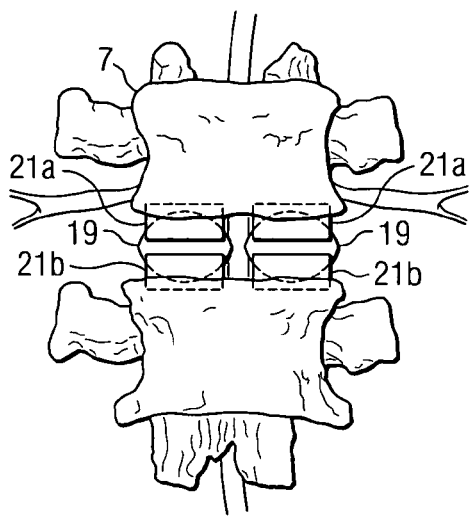
FIG. 5 is an anterior elevation view of a portion of a lumbar spine showing the superior, disc and inferior portions of the left and right halves of an assembled artificial intervertebral joint constructed according to the first embodiment of the disclosure.

FIGS. 4-7 illustrate a first exemplary embodiment of an artificial intervertebral joint. As illustrated in FIGS. 4 and 5, each joint is composed of two arthroplasty halves, each of which has a spacer or disc 19 and a retaining portion 21. The retaining portion 21 includes a first retaining portion 21a and a second retaining portion 21b. In the example illustrated in FIG. 4, the first retaining portion 21a is superior to (above) the second retaining portion 21b and the disc 19 is situated therebetween. Although the artificial intervertebral joint according to this exemplary embodiment has two halves for each of the first retaining portion and the second retaining portion, it should be understood that alternative embodiments may be implemented such that the artificial intervertebral joint has a single first retaining member, a single second retaining member and a single spacer. It should also be understood that alternative embodiments may also be carried out with arthroplasties having a first retaining portion, a second retaining portion, and/or a disc which each consist of unequal sized halves or more than two components.

Further, as illustrated in FIG. 4, the first retaining portion 21a and the second retaining portion 21b are situated between two adjacent vertebrae. More particularly, the first retaining portion may be situated along an inferior surface of the upper of the two adjacent vertebrae and the second retaining portion may be situated above a superior surface of the lower of the two adjacent vertebrae. However, it should be understood by one of ordinary skill in the art that the first retaining portion and second retaining portion are not limited to such an arrangement, and may be oriented in different positions and/or shaped differently than what is illustrated herein.

The surfaces of the retaining portions 21a, 21b of the arthroplasty that contact the remaining end plates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the implants to one or both of the endplates.

As discussed in more detail below, a significant portion of the outer annulus region 17 (see, e.g., FIGS. 4, 7B), in some embodiments about 300 degrees, may be retained on the inferior portion of the end plate, which acts as a stop retaining the lower retaining portions in place until bone ingrowth occurs to firmly attach the retaining portions to their respective vertebrae (FIG. 4 only shows a portion of the outer annulus 17 that is retained). In contrast, in conventional anterior arthroplasty about 270 degrees of the outer annulus region 17 typically is removed. In addition, pedicle screws may also be used for immediate fixation as described in more detail in connection with other embodiments discussed below.

In the various embodiments of this disclosure, the first retaining portion 21a and the second retaining portion 21b are structured so as to retain the disc 19 therebetween. For example, in the case of a disc 19 with two convex surfaces 19a, each of the first retaining portion 21a and the second retaining portion 21b may have a concave surface 21c which defines a space within which the disc 19 may be retained. For example, in the exemplary embodiment shown in FIG. 4, the upper convex surface 19a of the disc 19 fits within the concavity defined by the concave surface 21c of the first retaining portion 21a and the lower convex surface 19b of the disc 19 fits within the concavity defined by the concave surface 21c of the second retaining portion 21b.

Figure 6:
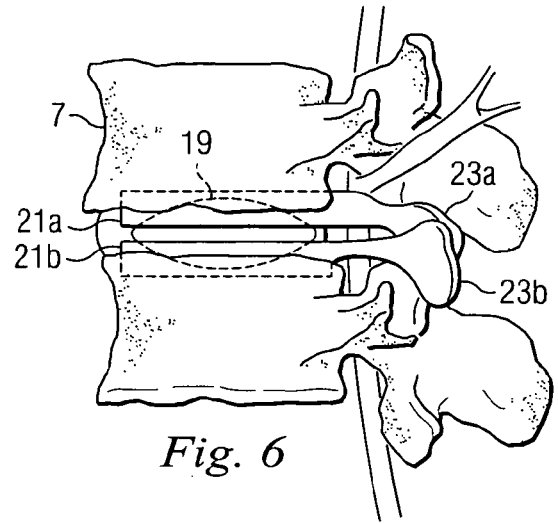
FIG. 6 is a side elevation view of the right half of the artificial intervertebral joint shown in FIG. 5.

FIG. 5 illustrates an anterior view of an exemplary assembled artificial intervertebral joint with both arthroplasty halves in place, and FIG. 6 shows a side view of the assembled artificial intervertebral joint shown in FIG. 5. As illustrated in FIGS. 5 and 6, the disc 19 is retained between the first retaining portion 21a and the second retaining portion 21b. It should be understood that although the disc 19 may be held between the first retaining portion 21a and the second retaining portion 21b, the disc 19 is free to slidably move within the space defined by the corresponding surfaces 21a of the first retaining portion 21a and the second retaining portion 21b. In this manner, limited movement between the adjacent vertebrae is provided.

In the exemplary embodiment illustrated in FIGS. 4, 5 and 6, the disc 19 is a separate component which is inserted between the first retaining portion 21a and the second retaining portion 21b. However, as discussed below, it should be understood that the spacer or disc 19 may be integrally formed with or integrated into in one or both of the first retaining portion 21a and the second retaining portion 21b.

Figure 7A:
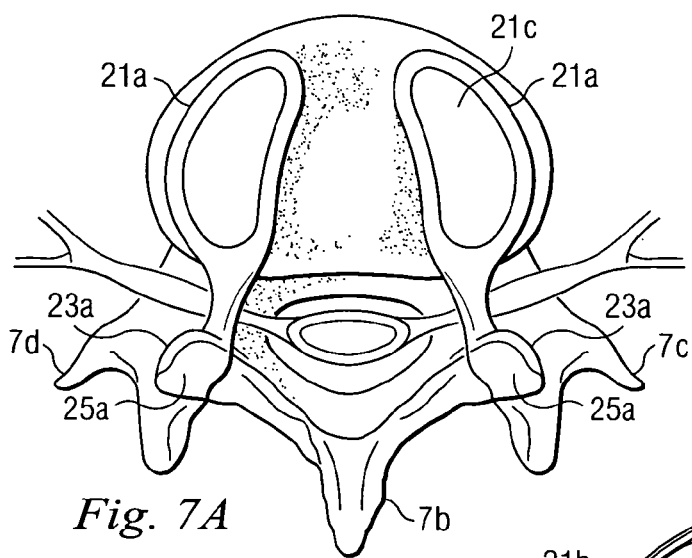
FIG. 7A is a transverse, bottom-up-view of a portion of a lumbar spine showing the superior portion of the artificial intervertebral joint illustrated in FIG. 4.
Figure 7B:
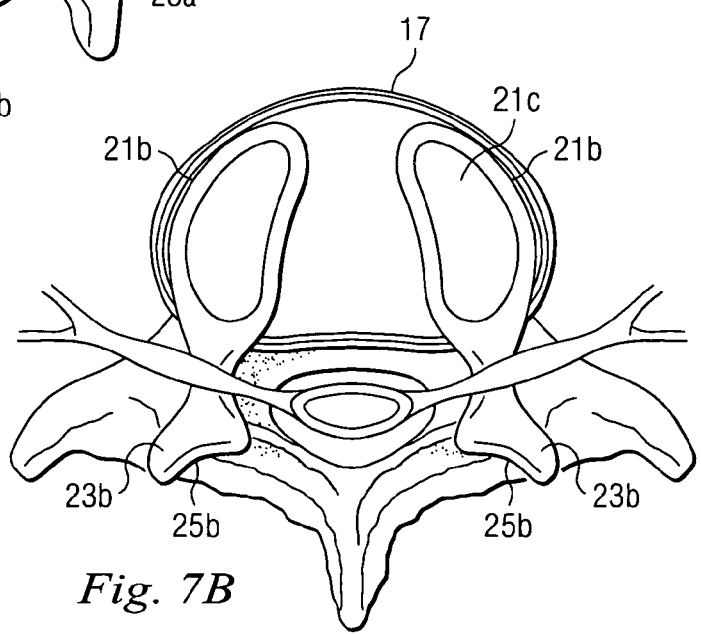
FIG. 7B is a transverse, top-down-view of a portion of a lumbar spine showing the inferior portion of the artificial intervertebral joint illustrated in FIG. 4.
Figure 8:
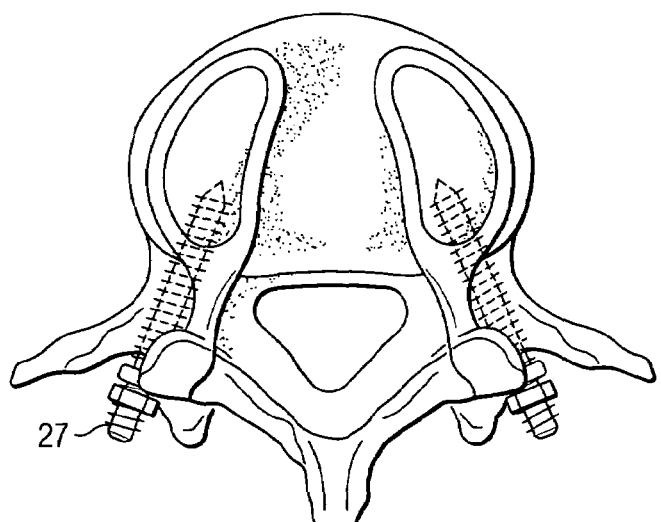
FIG. 8 is a transverse, bottom-up-view of a portion of a lumbar spine showing a second embodiment of a superior portion of an artificial intervertebral joint in which pedicle screws are used to assist in implantation.
Figure 9:
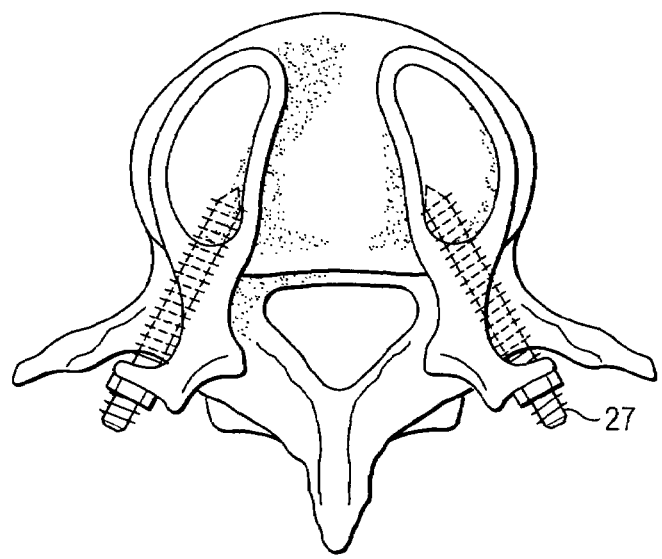
FIG. 9 is a transverse, top-down-view of a portion of a lumbar spine showing a second embodiment of an inferior portion of an artificial intervertebral joint in which pedicle screws are used to assist in implantation.
Figure 10:
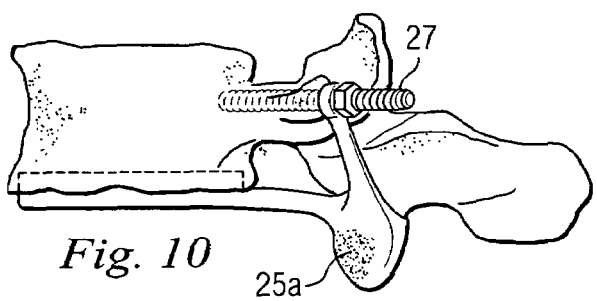
FIG. 10 is a lateral view of a portion of a lumbar spine showing the superior portion of the artificial intervertebral joint shown in FIG. 8 with one of the pedicle screws being visible.
Figure 11:
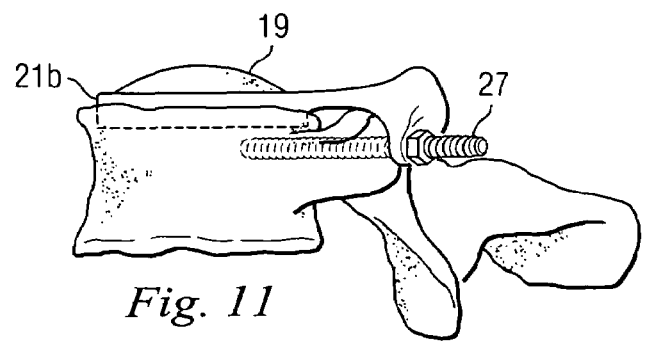
FIG. 11 is a lateral view of a portion of a lumbar spine showing the inferior and integrated disc portions of an artificial integral intervertebral joint shown in FIG. 9 with one of the pedicle screws being visible.
Figure 12:
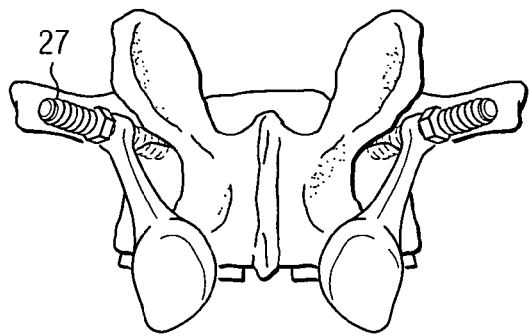
FIG. 12 is a posterior view of a portion of a lumbar spine showing the superior portion of the artificial intervertebral joint shown in FIG. 8 with two pedicle screws being visible.
Figure 13:
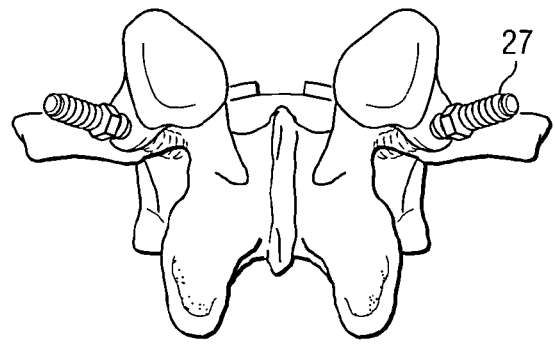
FIG. 13 is a posterior view of a portion of a lumbar spine showing the inferior portion of the artificial intervertebral joint shown in FIG. 9 with two pedicle screws being visible.
Figure 14:
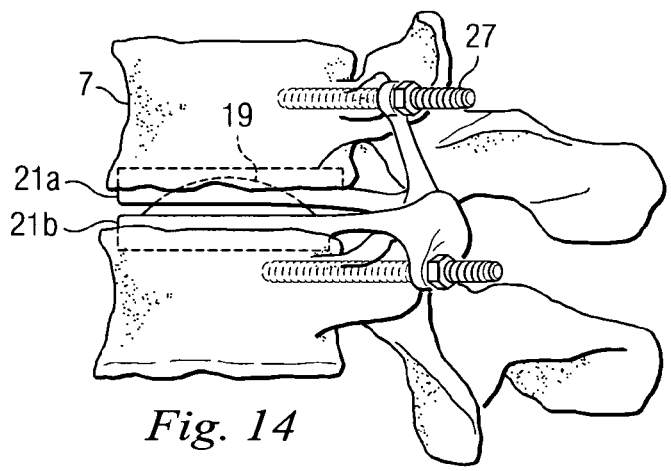
FIG. 14 is a side elevation view of a portion of a lumbar spine showing the second embodiment with pedicle screws in an assembled position.

In the exemplary embodiment of the disclosure, as illustrated best in FIGS. 4, 6, 7A and 7B, each of the retaining portions of the artificial intervertebral joint includes a first artificial facet component 23a and a second artificial facet component 23b. As shown in FIGS. 7A and 7B, the first artificial facet component 23a has a face 25a and the corresponding second artificial facet component 23b has a face 25b configured such that the face 25a matingly fits with the face 25b to stabilize adjacent vertebrae while preserving and guiding the mobility of each vertebrae with respect to the other vertebrae. Each set of the upper and lower retaining portions 21a, 21b may have a pair of facet components 23a, 23b, which together define a facet joint. For a total joint replacement with facets according to this embodiment, the left and right arthroplasties would define two adjacent facet joints when viewed from the posterior.

Regardless of whether artificial facet joints are provided, the respective upper and lower retaining portions associated with the left and right halves of the arthroplasty may be completely independent from the other. That is, as shown in FIG. 7A, for example, the first retaining portions 21a associated with each half are not in direct contact with each other. The same is true with respect to the second retaining portions 21b shown in FIG. 7B. However, it should be understood by one of ordinary skill in the art that, even in the embodiment of the disclosure which includes artificial facet joints, at least a portion of the first retaining portions 21a of each half and/or at least a portion of the second retaining portions 21b of each half may directly contact and/or be connected to each other as described in more detail in connection with the discussion of FIGS. 17-18.

Further, in the various embodiments of the disclosure, the disc 19, the first retaining portion 21a and the second retaining portion 21b may be made of any appropriate material which will facilitate a connection that transmits compressive and tensile forces while providing for the aforementioned slidable motion in a generally transverse direction between each of the adjacent surfaces. For example, in the first embodiment, the first retaining portion 21a and the second retaining portion 21b may be typically made from any metal or metal alloy suitable for surgical implants such as stainless steel, titanium, and cobalt chromium, or composite materials such as carbon fiber, or a plastic material such as polyetheretherketone (PEEK) or any other suitable materials. The disc may be made from plastic such as high molecular weight polyethylene or PEEK, or from ceramics, metal, and natural or synthetic fibers such as, but not limited to, carbon fiber, rubber, or other suitable materials. Generally, to help maintain the sliding characteristic of the surfaces, the surfaces may be polished and/or coated to provide smooth surfaces. For example, if the surfaces are made of metal, the metal surfaces may be polished metal.

FIGS. 8-14 illustrate a second embodiment of an artificial intervertebral joint. Only features that differ from the first embodiment are discussed in detail herein. In the second exemplary embodiment, securing components, such as, for example, pedicle screws 27 are provided to provide a more secure and immediate connection between each of the first retaining portion 21a and/or the second retaining portion 21b to the corresponding vertebra. In addition, this embodiment illustrates a disc 19 which is integrated with one of the retaining portions, here lower retaining portion 21b. Disc 19 may be integrally formed from the same material as its retaining portion, but also may be separately formed from similar or dissimilar materials and permanently connected thereto to form an integral unit. In this embodiment, the disc 19 and the retaining portions may be all formed from metal.

Figure 15:
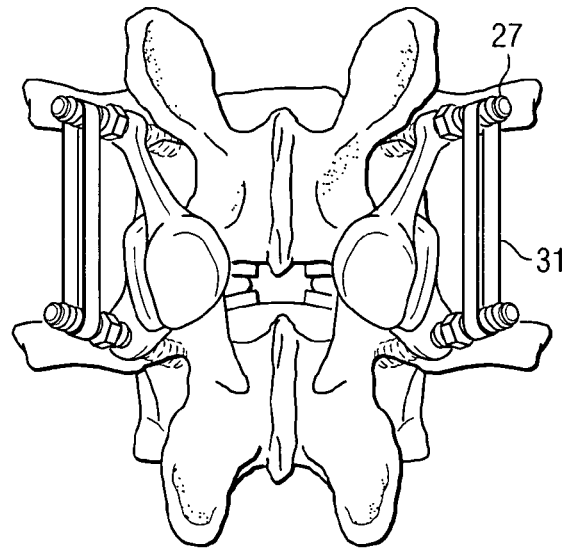
FIG. 15 is a posterior view of a portion of a lumbar spine showing a third embodiment of the inferior, disc and superior portions of an artificial intervertebral joint in which tension bands are used.
Figure 16:
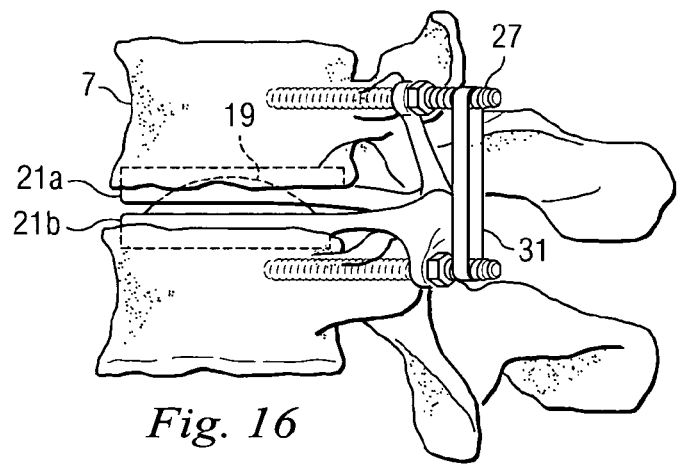
FIG. 16 is a side elevation view of a portion of a lumbar spine showing the third embodiment in which tension bands are used in an assembled position.

FIGS. 15 and 16 illustrate a third embodiment of an artificial intervertebral joint. In the third exemplary embodiment, additional securing components, such as, for example, tension bands 31 are provided to supplement or replace the function of posterior ligaments that limit the mobility between adjacent vertebrae by securing the first retaining portion 21a to the second retaining portion 21b. As shown in FIGS. 15-16, posterior tension bands 31 may be provided by wrapping them around the corresponding pedicle screws 27 or other convenient attachment points.

Figure 17:
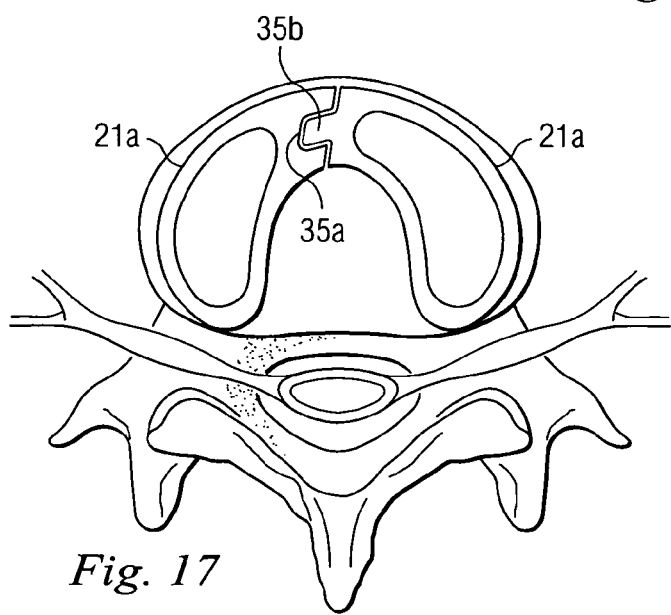
FIG. 17 is a transverse, bottom-up-view of a portion of a lumbar spine showing the superior portion of a fourth embodiment of an artificial intervertebral joint constructed according to the principles of the disclosure in which the facet joints are not replaced.
Figure 18:
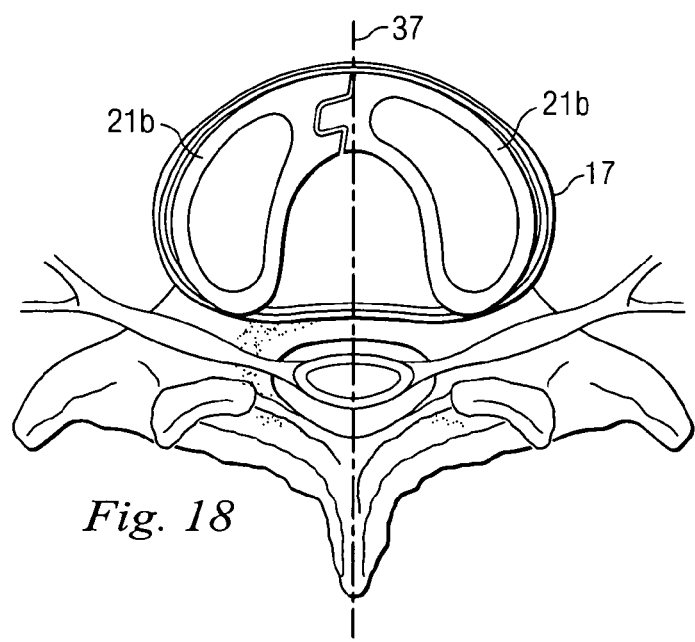
FIG. 18 is a transverse, top-down-view of a portion of a lumbar spine showing the inferior portion of the fourth embodiment of an artificial intervertebral joint.

FIGS. 17 and 18 illustrate a fourth embodiment of an artificial intervertebral joint. In the exemplary embodiment illustrated in FIGS. 17 and 18, the artificial intervertebral joint may have all of the features discussed above except for artificial facet components. In this embodiment, the natural facet joints remain. The ligamentous tension band may also be left intact in some embodiments. In addition, this embodiment includes a specific example of an anterior midline connection between respective upper and lower retaining portions, which assists in maintaining the placement of the first retaining portion 21a and the second retaining portion 21b.

FIGS. 17 and 18 illustrate that it is possible to provide a first retaining portion 21a with a lock and key type pattern which is complemented by the corresponding mating portion provided on the second retaining portion 21b. More particularly, one half of the first retaining portion 21a has an outer boundary with a U-shaped portion 35a while the other half of the corresponding first retaining portion 21a has an outer boundary with a protruding portion 35b, which fits into the U-shaped portion 35a. As a result, each half of the first retaining portion 21a, 21b may be maintained in a predetermined position. However, the upper or lower retaining portions may fit together and/or be connected in the interbody space, e.g., near their midline anterior portions, in any manner that facilitates implantation and/or assists in providing and/or retaining the joint in a generally stable, symmetrical configuration. It may be even more important to provide such connection between the lower retaining portions due to the inward forces provided by annulus 17 remaining on the inferior end plate as shown in FIG. 18. A midline connection between the respective lower retaining portions will resist the force of the outer annulus tending to cause migration of the retaining portions toward the midline 37.

As shown in the various exemplary embodiments, other than the portions of the first and/or second retaining portions which may fit together like a lock and key to maintain the placement of the portions relative to each other, each half of the artificial intervertebral joint may be generally symmetrical about the midline 37 of the vertebrae.

Again, these exemplary embodiments are merely illustrative and are not meant to be an exhaustive list of all possible designs, implementations, modifications, and uses of the invention. Moreover, features described in connection with one embodiment of the disclosure may be used in conjunction with other embodiments, even if not explicitly stated above.

While it should be readily apparent to a skilled artisan from the discussion above, a brief description of a suitable surgical procedure that may be used to implant the artificial joint is provided below. Generally, as discussed above, the artificial intervertebral joint may be implanted into a body using a posterior transforaminal approach similar to the known TLIF or PLIF procedures. According to this approach, an incision, such as a midline incision, may be made in the patient's back and some or all of the affected disc and surrounding tissue may be removed via the foramina. Depending on whether any of the facet joints are being replaced, the natural facet joints may be trimmed to make room for the artificial facet joints. Then, the halves of the artificial intervertebral joint may be inserted piecewise through the left and right transforaminal openings, respectively. That is, the pieces of the artificial intervertebral joint including the upper and lower retaining portions, with or without facet components, and the artificial disc, if provided separately, fit through the foramina and are placed in the appropriate intervertebral space. The pieces of the artificial joint may be completely separated or two or more of them may be tied or packaged together prior to insertion through the foramina by cloth or other materials known in the art. In cases where at least a portion of the outer annulus of the natural disc can be retained, the lower retaining portions of each side of the artificial intervertebral joint are inserted such that they abut a corresponding portion of the annulus. If a midline anterior connection is provided, the left and right halves of the retaining members are fitted together and held in place by the outer annulus. As such, the remaining portion of the annulus may be in substantially the same place as it was prior to the procedure.

Further, in the cases where the annulus of the natural disc must be removed completely or this is insufficient annulus remaining, it is possible, for example, to use the embodiment of the disclosure where the pedicle screws are implemented so as to be assured that the pieces of the artificial intervertebral joint remain in place. It should be understood by one of ordinary skill in the art that the artificial joint could be implanted via an anterior approach or a combined anterior and posterior approach, although the advantages of a posterior procedure would be limited. For example, some of the pieces of the artificial intervertebral joint may be inserted from an anterior approach and others posteriorly. The anteriorly and posteriorly placed portions could be fitted together similar to the embodiment shown in FIGS. 17 and 18.

Figure 19:
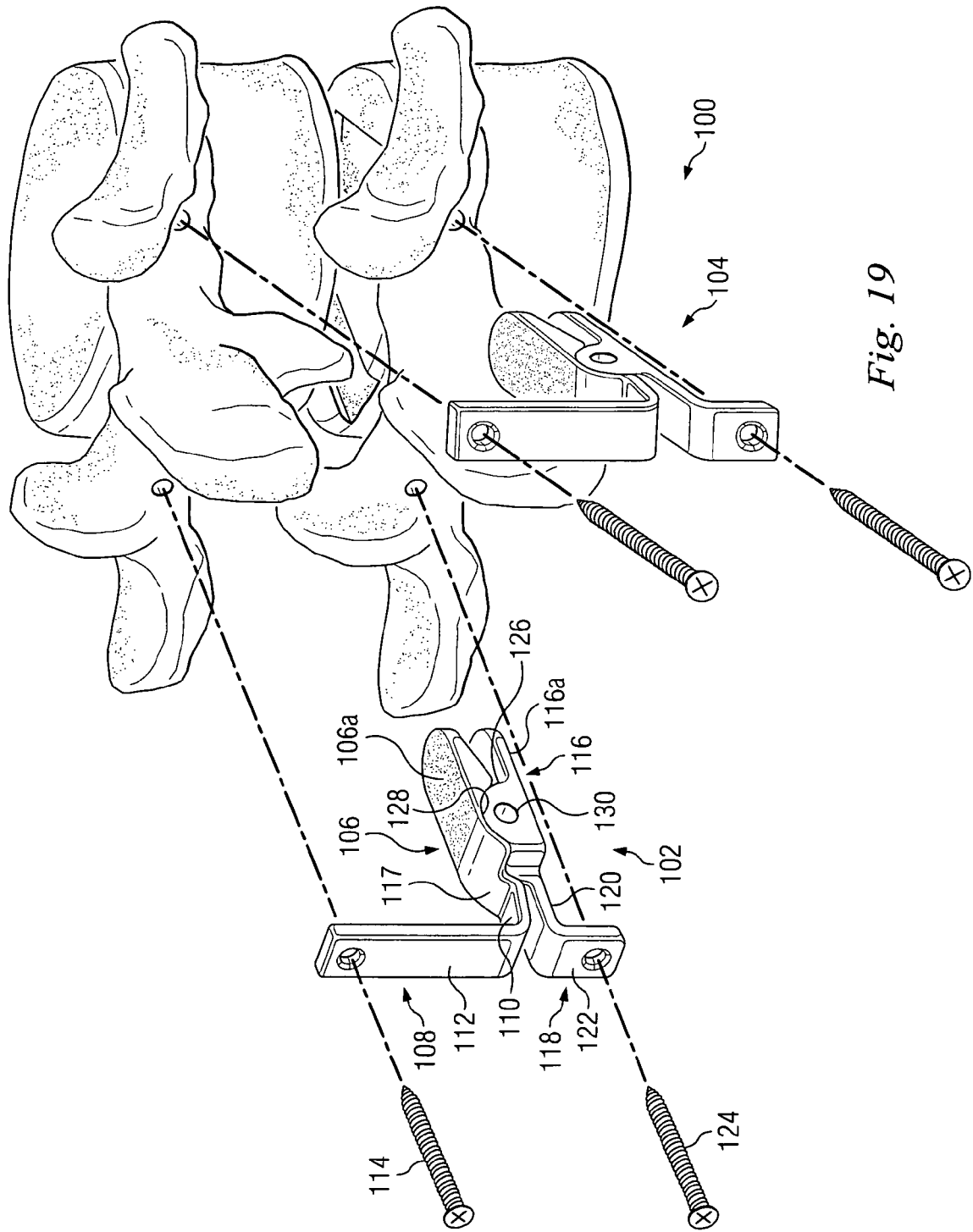
FIG. 19 is an exploded perspective view of an artificial vertebral joint according to another embodiment of the present disclosure.
Figure 20:
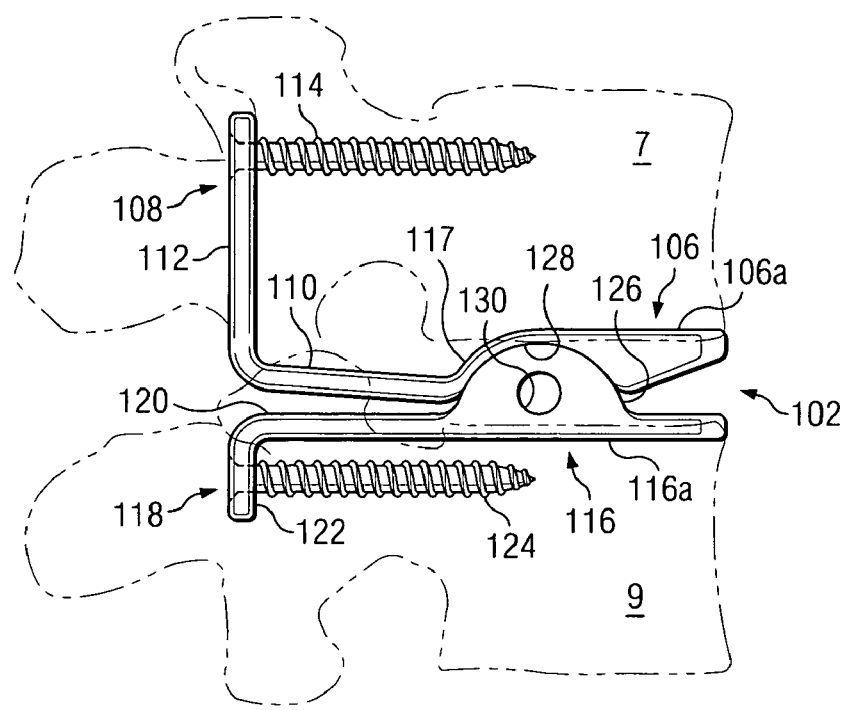
FIG. 20 is an assembled side view of the artificial vertebral joint of FIG. 19.

Referring now to FIGS. 19 and 20, in this embodiment, an artificial intervertebral joint 100 may include two joint halves 102, 104 which may be inserted between the vertebrae 7, 9. The joint half 104 may be substantially similar in structure and function to the joint half 102 and therefore will not be described in further detail. The joint half 102 may include a rostral anterior joint component 106, a rostral posterior connection assembly 108, and a rostral bridge 110 extending between the anterior component 106 and the posterior connection assembly 108. The rostral posterior connection assembly 108 may include a connection component 112 and a fastener 114. The joint half 102 may further include a caudal anterior joint component 116, a caudal posterior connection assembly 118, and a caudal bridge 120 extending between the anterior component 116 and the posterior connection assembly 118. The caudal posterior connection assembly 118 may include a connection component 122, such as tab, and a fastener 124. The rostral anterior joint component 106 may include a bone contacting surface 106a and the caudal anterior joint component 116 may include a bone contacting surface 116a. In this embodiment, the rostral bridge 110 may include a jog 117 to create an exit portal and an artificial foramen for the exiting nerve root. Either of the bridges 110, 120, but particularly the caudal bridge 120, may be a "super" or artificial pedicle which may supplement or replace a natural pedicle.

The terms "rostral" and "caudal" are used in some embodiments to describe the position of components of the embodiments. While rostral is typically used in the art to describe positions toward the head and caudal is used to describe positions toward the tail or foot, as used herein, rostral and caudal are used simply as modifiers for the relative locations of components of the illustrated embodiments. For example, rostral components may be on one side of an illustrated joint, and caudal may be on another side of the joint. Components labeled as rostral or caudal to describe an illustrated embodiment are not intended to limit the orientation of a device or application of a method relative to a patient's anatomy, or to limit the scope of claims to any device or method.

Also in this embodiment, the caudal anterior joint component 116 may include a semi-cylindrical protrusion 126, and the rostral anterior joint component 106 may include an anterior recess 128 configured to receive the semi-cylindrical protrusion 126 to form an articulating assembly. A bore 130 may extend laterally through the semi-cylindrical protrusion 126. A radius of curvature for the semi-cylindrical protrusion 126 may closely match the radius of curvature for the anterior recess 128 to create a highly constrained articulating assembly. In an alternative embodiment, by increasing the radius of curvature for the recess relative to the radius of the semi-cylindrical protrusion, the semi-cylindrical protrusion may be permitted to translate within the recess. In still another alternative, the protrusion may be domed with a recess to match. In still another alternative, the protrusion may have curved lateral edges to permit lateral bending.

The connection component 112 may-be a tab through which the fastener 114 may extend. The tab may include an aperture, a U-shaped slot, a C-shaped slot or any type of holder for accepting the fastener 114. The connection component 122 may be similarly configured to accept the fastener 124. The fasteners 114, 124 may be pedicle screws, but other types of fasteners such as bolts, forks, spikes, latches, or adhesives may be used. In all embodiments, the fasteners may be recessed so as not to interfere with articulations, soft tissues, and neural structures. It is understood that in other alternative embodiments, the connection components may extend at a variety of angles, in a variety of directions from the various components of the joint half. For example, a connection component may extend from the rostral bridge rather than the rostral anterior joint component.

The size and shape of the anterior components 106, 116 and the bridge components 110, 120 may be limited by the constraints of a posterior or transforaminal surgical approach. For example, the anterior components 106, 116 may be configured to cover a maximum vertebral endplate area to dissipate loads and reduce subsidence while still fitting through the posterior surgical exposure, Kambin's triangle, and other neural elements. To achieve maximum surface coverage, the material of the anterior components 106, 116 may extend anteriorly from the semi-cylindrical protrusion 126 and the anterior recess 128, respectively. The width of the bridge components 110, 120 are also minimized to pass through Kambin's triangle and to co-exist with the neural elements.

As shown in FIGS. 19 and 20, the rostral components 106, 108, 110 of the joint half 102 are integrally formed. It is understood that in a modular alternative embodiment, these components may be removably coupled to one another. For example, the rostral anterior joint component may be installed separate from the bridge. After the anterior component is in place, the bridge may be attached to the anterior component by any fastening mechanism known in the art, for example a threaded connection, a bolted connection, or a latched connection. A modular rostral posterior component may then be attached by a similar fastening mechanism to the bridge to complete the rostral portion of the joint half. Likewise, the caudal components may also be modular.

The joint halves 102, 104 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the joint halves 102, 104 may be formed of different materials thus permitting metal on metal, metal on ceramic, metal on polymer, ceramic on ceramic, ceramic on polymer, or polymer on polymer constructions.

Bone contacting surfaces of the joint halves 102, 104 may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the joint halves 102, 104 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The artificial intervertebral joint 100 may be installed between the vertebrae 7, 9 as will be described below. Although installation will be described with respect to joint half 102, it is understood that the joint half 104 may be installed in a similar manner. Generally, as discussed above, the artificial intervertebral joint 100 may be implanted into a body using a posterior transforaminal approach similar to the known TLIF or PLIF procedures.

PLIF approaches are generally more medial and rely on more retraction of the traversing root and dura to access the vertebral interspace. The space between these structures is known as Kambin's triangle. TLIF approaches are typically more oblique, requiring less retraction of the exiting root, and less epidural bleeding with less retraction of the traversing structures. It is also possible to access the interspace using a far lateral approach, above the position of the exiting nerve root and outside of Kambin's triangle. In some instances it is possible to access the interspace via the far lateral without resecting the facets. Furthermore, a direct lateral approach through the psoas is known. This approach avoids the posterior neural elements completely. Embodiments of the current invention are anticipate that could utilize any of these common approaches.

According to at least one of these approaches, an incision, such as a midline incision, may be made in the patient's back and some or all of the affected disc and surrounding tissue may be removed via the foramina. Primary and secondary stabilizers may also be resected. The fasteners 114, 124 may be connected to the vertebrae 7, 9, respectively. In this embodiment, the fasteners 114, 124 are pedicle screws threaded into the pedicles of vertebrae 7, 9, respectively.

The superior endplate surface of the vertebra 9 may be milled, rasped, or otherwise resected to match the profile of the caudal anterior bone contacting surface 116*a*, to normalize stress distributions on the superior endplate surface of the vertebra 9, and/or to provide initial fixation prior to bone ingrowth. The preparation of the endplate of vertebra 9 may result in a flattened surface or in surface contours such as pockets, grooves, or other contours that may match corresponding features on the bone contacting surface 116*a*. The inferior endplate of the vertebra 7 may be similarly prepared to receive the rostral anterior joint component 106 to the extent allowed by the exiting nerve root and the dorsal root ganglia. To accomplish the resection, a cutting guide (not shown) may be connected to one or both fasteners 114, 124. Through this cutting guide, a cutting instrument such as an osteotome, milling burr, rasp, or any other sharp or abrasive instrument may be inserted. The cutting instrument may be used to resect only one vertebral endplate, both vertebral endplates simultaneously or both vertebral endplates serially. The natural facet joints of vertebrae 7, 9 may be trimmed to make room for the posterior connection assemblies 108, 118.

With the endplate(s) prepared, the cutting guide may be removed from the fasteners 114, 124. The halves 102, 104 of the artificial intervertebral joint 100 may then be inserted piecewise through the left and right transforaminal openings, respectively. That is, the pieces of the artificial intervertebral joint 100 including the rostral and caudal anterior joint components 106, 116 respectively fit through the foramina and are placed in the appropriate intervertebral disc space between the generally cylindrical bodies 7*a*, 9*a*. The pieces of the artificial joint 100 may be completely separated or two or more of them may be tied or packaged together prior to insertion through the foramina by cloth or other materials known in the art. Once the rostral anterior joint component 106 and the caudal anterior joint component 116 are inserted into the intervertebral disc space, the semi-cylindrical protrusion 126 may be placed into articulating engagement with the anterior recess 128. In cases where at least a portion of the outer annulus of the natural disc can be retained, the caudal anterior joint components of each side of the artificial intervertebral joint are inserted such that they abut a corresponding portion of the annulus. The bridges 110, 120 may extend posteriorly from the anterior joint components 106, 116 and posteriorly from the intervertebral disc space. The posterior connection assemblies 108, 118 are positioned posteriorly of the intervertebral disc space. Because the cutting guide and the joint half 102 may be indexed to the same fastener locations, alignment of the joint half 102, particularly alignment of the semi-cylindrical and recess components, within the intervertebral disc space may be simplified and more accurate. It is understood that in some embodiments, the cutting guide may also serve as a window for inserting the halves 102, 104, and thus the cutting guide or another guiding member may remain attached to the fasteners during the implantation of the artificial joint.

The angled facet geometry of the patient may determine a proper approach angulation for connector components 112, 122. The connector components may be adjustable to match the natural or resected angulation or a selection of connector components may be provided. The connection components 112, 122 may then be attached to the fasteners 114, 124, respectively. The bore 130 may be laterally aligned with a corresponding bore on the joint half 104 using fluoroscopic imaging. With the halves 102, 104 properly in place, the fasteners 114, 124 may be tightened to lock the joint half 102 into place. The corresponding fasteners for half 104 may also be tightened to lock the joint half 104 into place.

As installed, the anterior joint created by the rostral anterior joint component 106 and the caudal anterior joint component 116 may be relatively stable and self-centering. The semi-cylindrical protrusion 126 engaged with the anterior recess 128 may be generally constrained to flexion-extension motion and may resist shear loading in the anterior-posterior direction, rotational movement, and lateral bending. The joint 100 is thus stable despite massive resection of the primary and secondary stabilizers. Flexion-extension motion may be constrained to within five degrees of extension and fifteen degrees of flexion. Under certain conditions, the joint 100 may overcome the built-in design restrictions to permit limited lateral, rotational, and coupled movements. For example, the anterior joint components 106, 116 may become partially or entirely disengaged from each other and experience limited "lift-off," thereby permitting additional degrees of freedom and coupled motions beyond strict flexion-extension motion. The self-centering nature of the anterior joint may encourage reengagement and alignment after lift-off occurs.

Figure 21:
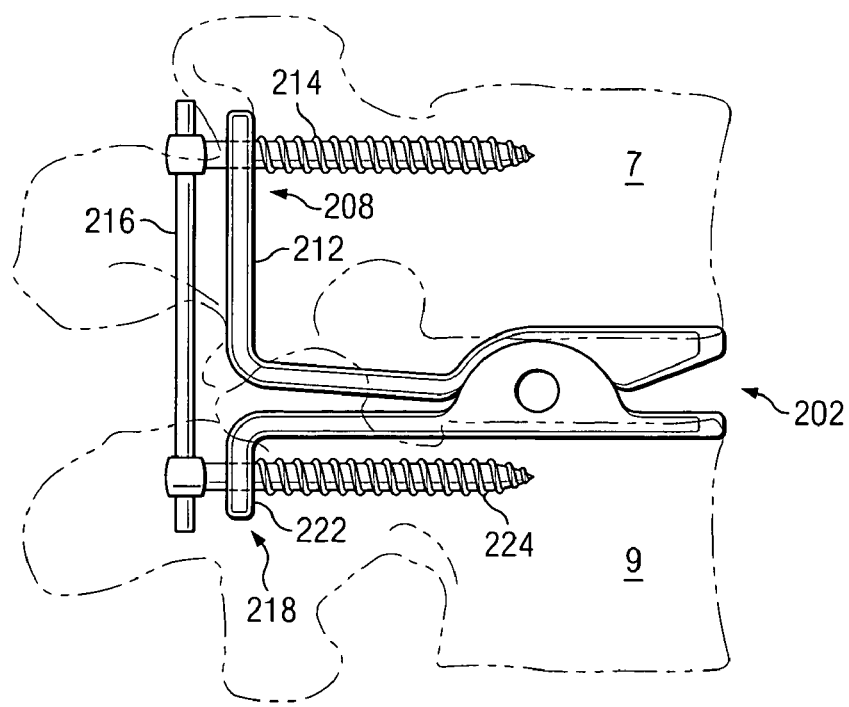
FIG. 21 is an assembled side view of an artificial vertebral joint according to another embodiment of the present disclosure.

Referring now to FIG. 21, in another embodiment, a joint half 202 and its components may be substantially similar to joint 102 and the installation methods described above except for the differences described below. The joint half 202 may include a rostral posterior connection assembly 208 and a caudal posterior connection assembly 218. The rostral posterior connection assembly 208 may include a connection component 212 and a fastener 214, and the caudal posterior connection assembly 218 may include a connection component 222 and a fastener 224. The connection component 212 may be a tab through which the fastener 214 may extend. The tab may include an aperture, a U-shaped slot, a C-shaped slot or any type of holder for accepting the fastener 214. The connection component 222 may be similarly configured to accept the fastener 224. In this embodiment, the fasteners 214, 224 may be multi-axial pedicle screws.

To resist shear loading of the anterior vertebral column, a constraint component 216 may extend between the fasteners 214, 224 to provide either semi-compliant constraint which would allow limited motion in the joint 100 or rigid constraint to fuse the joint 100. The constraint provided by the constraint component 216 may eliminate the need for the natural facet joints. The constraint component 216 may be a compliant rod formed of a polymer such as PEEK or any of the other polymers listed above. The constraint component 216 may, alternatively, be a rod formed of a rigid metal such as titanium. The rod 216 may inserted through the multi-axial pedicle screw fasteners 214, 224. The multi-axial nature of the pedicle screw allows for three dimensional adjustment to accommodate the patient's particular anatomy. In an alternative embodiment, the constraint component may be a rigid plate. In still another alternative, the constraint component may be an elastomeric band.

The constraint component 216 may be installed when the joint half 202 is originally installed or may be it may be installed as part of a revision procedure. When it is installed as part of a revision procedure, the joint half 202 may be installed as described above for joint half 102. At a later time, when the patient's spine has deteriorated further, the patient may undergo a revision procedure in which a second incision is made to access the joint half 202. The constraint component may then be connected to existing fasteners or the fasteners may be replaced. The constraint component a may be selected based upon the desired amount of constraint. If a compliant rod is selected as the constraint component, still further revision surgeries may be performed to trade the compliant rod for a rigid rod.

In an alternative embodiment, any of the artificial intervertebral joints described above may further include a rostral keel extending from the rostral anterior component and/or a caudal keel extending from the caudal anterior joint component and along the caudal bridge. The rostral keel may engage the inferior endplate of the vertebral body 7a, and the caudal keel may engage the superior endplate of the vertebral body 9a and a superior face of a pedicle of vertebra 9. It is understood that the inferior endplate of the body 7a may be milled or otherwise prepared to receive the rostral keel. Likewise, the superior endplate of the body 9a and the pedicle of vertebra 9 may be milled, chiseled, or otherwise prepared to create a channel for receiving the caudal keel. The keels may help to connect to the bone and limit movement of the arthroplasty half to the desired degrees to freedom. The keels may have an angled or semi-cylindrical cross section. It is understood that more than one keel may be used on any given component.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An artificial spinal joint for creating at least a portion of a coupling between a superior vertebra and an inferior vertebra, the artificial spinal joint comprising:
   a first joint half comprising a first intervertebral articulating assembly, a first rostral connection assembly, and a first caudal connection assembly, wherein the first intervertebral articulating assembly comprises a first semi-cylindrical component and a first recess, and wherein the first semi-cylindrical component is shaped for articulating engagement with the first recess, and wherein the first rostral connection assembly is cooperatively connected to and positioned posteriorly from the first articulating assembly such that the first rostral connection assembly is located posterior to the pedicles of a superior vertebra when the first articulating assembly is in an intervertebral disc space, and wherein the first caudal connection assembly is cooperatively connected to and positioned posteriorly from the first articulating assembly such that the first caudal connection assembly is located posterior to the pedicles of an inferior vertebra when the first articulating assembly is in the intervertebral disc space;
   a second joint half unconnected and spaced apart from the first joint half and comprising a second intervertebral articulating assembly, a second rostral connection assembly, and a second caudal connection assembly, wherein the second intervertebral articulating assembly comprises a second semi-cylindrical component and a second recess, and wherein the second semi-cylindrical component is shaped for articulating engagement with the second recess; and
   a constraint component extending between the first rostral connection assembly and the first caudal connection assembly.

2. The artificial spinal joint of claim 1 wherein the first rostral connection assembly comprises a rostral connection component shaped to receive a rostral fastener and the first caudal connection assembly comprises a caudal connection component shaped to receive a caudal fastener.

3. The artificial spinal joint of claim 2 wherein the rostral and caudal fasteners are pedicle screws.

4. The artificial spinal joint of claim 3 wherein the pedicle screws are multi-axial pedicle screws.

5. The artificial spinal joint of claim 2 wherein the constraint component comprises a rod extending from the rostral fastener to the caudal fastener.

6. The artificial spinal joint of claim 5 wherein the rod is compliant.

7. The artificial spinal joint of claim 5 wherein the rod is non-compliant.

8. The artificial spinal joint of claim 5 wherein the rod comprises PEEK.

9. The artificial spinal joint of claim 5 wherein the rod comprises titanium.

10. The artificial spinal joint of claim 2 wherein the constraint component comprises a rigid plate attached to the rostral and caudal fasteners.

11. The artificial spinal joint of claim 2 further comprising an elastomeric band extending between the rostral and caudal fasteners.

12. The artificial spinal joint of claim 2 wherein the caudal connection component is adjustable.

13. The artificial spinal joint of claim 1 wherein the first and second semi-cylindrical components each comprise lateral through bores for aligning the first and second joint halves under fluoroscopic guidance.

14. The artificial spinal joint of claim 1 wherein the first semi-cylindrical component and the first recess articulate to approximately five degrees extension.

15. The artificial spinal joint of claim 1 wherein the first semi-cylindrical component and the first recess articulate to approximately fifteen degrees flexion.

16. The artificial spinal joint of claim 1 wherein the first joint half further comprises a first surface extending beyond the first semi-cylindrical component.

17. An artificial spinal joint for creating at least a portion of a coupling between a superior vertebra and an inferior vertebra adjacent an intervertebral disc space, the artificial spinal joint comprising:
   a first joint half comprising a first intervertebral articulating assembly, a first rostral connection assembly, and a first caudal connection assembly, wherein the first joint half further includes a jog configured in a manner that permits passage of a neural element, and wherein the first rostral connection assembly is cooperatively connected to and positioned posteriorly from the articulating assembly such that the first rostral connection assembly is located posterior to the pedicles of the superior vertebra when the first articulating assembly is in the intervertebral disc space, and wherein the first caudal connection assembly is cooperatively connected to and positioned posteriorly from the articulating assembly such that the first rostral connection assembly is located posterior to the pedicles of the inferior vertebra when the first articulating assembly is in the intervertebral disc space;

a second joint half unconnected and spaced apart from the first joint half and comprising a second intervertebral articulating assembly, a second rostral connection assembly, and a second caudal connection assembly; and a constraint component extending from the first rostral connection assembly to the first caudal connection assembly.

18. An artificial spinal joint for creating at least a portion of a coupling between a superior vertebra and an inferior vertebra adjacent an intervertebral disc space, the artificial spinal joint comprising:

a first joint half comprising a first intervertebral articulating assembly, a first rostral connection assembly, and a first caudal connection assembly, wherein the first intervertebral articulating assembly comprises a first semi-cylindrical component and a first recess, and wherein the first semi-cylindrical component and the first recess are configured to become temporarily disconnected during a lateral bending motion, and wherein the first rostral connection assembly is cooperatively connected to and positioned posteriorly from the articulating assembly such that the first rostral connection assembly is located posterior to the pedicles of the superior vertebra when the first articulating assembly is in the intervertebral disc space, and wherein the first caudal connection assembly is cooperatively connected to and positioned posteriorly from the articulating assembly such that the first caudal connection assembly is located posterior to the pedicles of the inferior vertebra when the first articulating assembly is in the intervertebral disc space;

a second joint half unconnected and spaced apart from the first joint half and comprising a second intervertebral articulating assembly, a second rostral connection assembly, and a second caudal connection assembly; and a constraint component extending from the first rostral connection assembly to the first caudal connection assembly.

19. An artificial joint system locatable between an upper vertebra and a lower vertebra, the system comprising:

an articulating assembly for interposition in an intervertebral disc space, the articulating assembly comprising a first articulating component movable with respect to a second articulating component;

a first bridge component coupled to the first articulating component and sized to extend posteriorly past the pedicles of the upper and lower vertebrae from the intervertebral disc space when the articulating assembly is in the intervertebral disc space;

a first connection assembly coupled to the first bridge component;

a second bridge component coupled to the second articulating component and sized to extend posteriorly past the pedicles of the upper and lower vertebrae from the intervertebral disc space when the articulating assembly is in the intervertebral disc space;

a second connection assembly coupled to the second bridge component, wherein the first connection assembly includes a first connection tab and a first pedicle screw, the first pedicle screw extending through the first connection tab and the second connection assembly includes a second connection tab and a second pedicle screw, the second pedicle screw extending through the second connection tab; and a constraint component extending from the first pedicle screw to the second pedicle screw.

20. The artificial joint system of claim 19 wherein the constraint component includes a rod shaped to extend between the first pedicle screw and the second pedicle screw.

21. The artificial joint system of claim 20 wherein the rod is adjustable in three dimensions.

22. The artificial joint system of claim 20 wherein the first and second pedicle screws are multiaxial pedicle screws.

23. The artificial joint system of claim 20 wherein the rod is formed of a compliant material.

24. The artificial joint system of claim 20 wherein the rod is formed of a rigid material.

25. The artificial spinal joint of claim 19 wherein the first bridge component is at least a portion of an artificial pedicle.

26. A system for implantation between upper and lower vertebrae comprising:

a first joint half including,
a first upper component including a first articulation surface,
a first lower component including a second articulation surface in movable engagement with the first articulation surface, the first and second articulation surfaces being configured to be placed within an intervertebral disc space between upper and lower vertebrae, the first upper and the first lower components respectively including a first extending upper portion and a first extending lower portion, the first extending upper portion and the first extending lower portion being sized to extend posteriorly from the intervertebral disc space and extend between pedicles of the upper and lower vertebrae when the articulation surfaces are within the intervertebral disc space,
a first threaded connector configured for insertion into a pedicle of the upper vertebra through the posterior extending portion of the first upper component, and
a second threaded connector configured for insertion into a pedicle of the lower vertebra through the posterior extending portion of the first lower component;

a second joint half including,
a second upper component separated from the first upper component and including a third articulation surface,
a second lower component including a fourth articulation surface in movable engagement with the third articulation surface, and a constraint component extending between a portion of the first threaded connector and a portion of the second threaded connector outside of an intervertebral disc space defined between the upper and lower vertebrae.

27. The system of claim 26 wherein the constraint component comprises a rod extending from the first threaded connector to the second threaded connector.

28. The system of claim 27 wherein the rod is compliant.

29. The system of claim 27 wherein the rod is non-compliant.

30. The system of claim 27 wherein the rod comprises PEEK.

31. The system of claim 27 wherein the rod comprises titanium.

32. The system of claim 26 wherein the constraint component comprises a rigid plate attached to the rostral and caudal fasteners.

33. The system of claim 26 further comprising an elastomeric band extending between the rostral and caudal fasteners.

34. The system of claim 26 wherein the caudal connection component is adjustable.

35. The system of claim 26 wherein one of the first upper and lower components and one of the second upper and lower components comprise a lateral through bore for aligning the first and second joint halves under fluoroscopic guidance.

36. The system of claim 26 wherein the constraint component includes a rod shaped to extend between the first threaded connector and the second threaded connector.

37. The system of claim 36 wherein the rod is adjustable in three dimensions.

38. The system of claim 26 wherein the first and second threaded connectors are multiaxial pedicle screws.

* * * * *